US00PP12505P2

(12) United States Plant Patent
Slaughter et al.

(10) Patent No.: US PP12,505 P2
(45) Date of Patent: Apr. 2, 2002

(54) PEACH TREE NAMED 'BURPEACHFIVE'

(75) Inventors: John K. Slaughter, Clovis; Timothy J. Gerdts, Kingsburg, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/455,972

(22) Filed: Dec. 6, 1999

(51) Int. Cl.[7] ..... A01H 5/00
(52) U.S. Cl. ..... Plt./198

(58) Field of Search ..... Plt./198

*Primary Examiner*—Bruce R. Campell
*Assistant Examiner*—Susan B. McCormick
(74) *Attorney, Agent, or Firm*—Wells, St. John, Roberts, Gregory & Matkin, P.S.

(57) ABSTRACT

A new and distinctive variety of peach tree denominated varietally as 'Burpeachfive', and which is characterized as to novelty by a date of maturity for commercial harvesting and shipment of, approximately June 27 to July 10 under the ecological conditions prevailing in the San Joaquin Valley of Central California.

1 Drawing Sheet

BACKGROUND OF THE NEW VARIETY

The present invention relates to a new, novel and distinct variety of peach tree, which has the denominated varietally as 'Burpeachfive'. The 'Burpeachfive' Peach Tree produces an exceptionally high quality, freestone peach which matures in the middle of the season. Another unique aspect of the 'Burpeachfive' is that it yields an exceptionally firm peach that exhibits very high eating quality as compared with the other freestone peach varieties which mature at approximately the same time of the season.

ORIGIN

The present peach tree was the result of an ongoing program of fruit and nut tree breeding. The purpose of this program is to improve the commercial selections of prunus, malus and regia species. To this end, we make both controlled and hybrid crosses each year in order to produce seedling populations from which improved progenies are evaluated and selected.

The seedling 'Burpeachfive' was originated by us in 1994, and chosen from among a population of seedlings which resulted from a controlled cross of an unnamed peach seedling, used as the seed parent, and the 'Grand Diamond' nectarine, (U.S. Plant Pat. No. 4,095), which was used as the pollen parent. Resulting seed from this cross were planted in the spring of 1995. The new variety was selected from among seedlings growing in the experimental orchards of The Burchell Nursery, Inc. near the city of Fowler, Calif., County of Fresno, in the Central portion of the San Joaquin Valley of California. The 'Burpeachfive' was marked for subsequent observation and noted as having exceptional characteristics. It was subsequently evaluated during the 1996–1999 fruit growing seasons. After the 1996 season, 'Burpeachfive' was selected for advanced evaluation and repropagation.

ASEXUAL REPRODUCTION

Scionwood from the original seedling of the 'Burpeachfive' peach, was collected and grafted onto two different and existing 'Nemared' unpatented peach rootstocks in February 1997 in the evaluation plot on The Burchell Nursery's experimental farm previously described. Fruit from the resulting propagation has been evaluated for the 1998–2000 fruit seasons. This evaluation clearly demonstrated that the repropagated trees are true to the characteristics of the original seedling in all observable aspects.

SUMMARY OF THE VARIETY

The 'Burpeachfive' peach is characterized as to novelty and is otherwise noteworthy by producing fruit which ripens in mid-season; is considered very high quality; and which further is very firm and has an attractive coloration. In this regard, the present variety of peach tree bears fruit which are ripe for commercial harvesting and shipment in approximately the last days of June and/or the first days of July. This is approximately the same harvesting period as the common commercial freestone Peach variety named 'Flamecrest'. However, the present variety is distinguishable from the 'Flamecrest' by its highly colored skin, exceptionable firmness and extremely flavorful flesh quality.

BRIEF DESCRIPTION OF THE DRAWING

The accompanying drawing is a color photograph of a characteristic twig bearing typical leaves; several leaves showing both the dorsal and ventral coloration, and several mature fruit showing their external coloration sufficiently matured for harvesting and shipment. Additionally, one fruit of the subject variety is dissected in the equatorial or cheek plane to illustrate the flesh and stone characteristics thereof.

DETAILED DESCRIPTION

Referring more specifically to the pomological details of this new and distinct variety of peach tree, the following has been observed under the ecological conditions prevailing near the town of Fowler, county of Fresno, state of California in 1998 and 1999. All major color code designations are by reference to The R.H.S. Colour Chart (Third Edition) provided by The Royal Horticultural Society of Great Britain.

Tree:

*Size.*—Generally — Average to above average as compared to other common peach cultivars.

*Productivity.*—Productive. Productivity with respect to pounds per acre is not available.

*Figure.*—The original seedling was trained in a central leader configuration with a moderate spread in the crown of the tree. The tree is considered upright to upright spreading in form.

*Height.*—The original seedling had a height dimension of 3.5 m at the end of the 1999 growing season.

*Width.*—The original seedling tree had a width of 2.19 m at the end of the 1999 growing season.

*Current season growth.*—The current season growth for the new variety was approximately 0.91–1.13 m.

*Regularity of bearing.*—Regular, and considered hardy under typical central San Joaquin Valley conditions.

Trunk:

*Diameter.*—Approximately 80 mm in diameter when measured at a distance of approximately 15.24 cm above the soil level, at the end of the 1999 growing season.

*Bark texture.*—Considered moderately rough with numerous folds of papery scarf skin being present.

*Lenticels.*—Numerous flat, oval lenticels are present. The lenticels range in size from approximately 2.5 to 7.1 millimeters in width and from approximately 1 to 2 millimeters in height.

*Bark coloration.*—Variable, but it is generally considered to be a greyed orange (RHS Greyed Orange Group 166 B).

Branches:

*Size.*—Considered medium for the variety.

*Diameter.*—The branches have a diameter of 55 to 60 mm when measured during the 3$^{rd}$ year following grafting.

*Surface texture.*—Average, and appearing furrowed on wood which is several years old.

*Crotch angles.*—Variable between about 43° to 57° from the horizontal axis for scaffold limbs. This is not distinctive of the variety, however.

*Current season shoots.*—Surface texture — Substantially glabrous.

*Internode length.*—Approximately 2.3 to 2.5 cm.

*Color mature branches.*—Medium brown, (RHS Grey Orange Group 166 D to 200 D).

*Current season shoots.*—Color — Light green, (RHS Yellow Green Group 145 B), with some reddish-brown coloration. Appearing on exposed exterior shoots (RHS Grey Red Group 181 B). The color of new shoot tips is considered a bright and shiny green (RHS Green Group 143 B).

Leaves:

*Size.*—Considered relatively large for the species. Leaf measurements have been taken from vigorous upright current season growth approximately at mid-shoot.

*Leaf length.*—Approximately 175 to 180 millimeters.

*Leaf width.*—Approximately 53 to 56 millimeters.

*Leaf thickness.*—Approximately 1 to 2 millimeters.

*Leaf base shape.*—The leaf base shape is slightly oblique.

*Leaf form.*—Lancelolate.

*Leaf tip form.*—Acuminate. The tip often appears flexed downwards and twisted laterally.

*Leaf color.*—Dark green, (RHS Green Group 137 A).

*Leaf texture.*—Substantially glabrous.

*Lower surface.*—Yellow-green, (RHS Yellow-Green Group 146 B).

*Venation.*—Primarily net veined.

*Mid-vein.*—Color — Light yellow green, (RHS Yellow Green Group 150 D).

*Leaf margins.*—Form — Considered crenate, occasionally doubly crenate. Uniformity — Considered generally uniform.

*Leaf petioles.*—Size — Considered medium. Length — Approximately 5 to 9 millimeters. Diameter — Approximately 1.5 to 2 millimeters. Color — Pale green, (RHS Yellow Green Group 145 D).

*Leaf glands.*—Size — Approximately one to two millimeters in height and two to three millimeters in width. Numbers — Generally 2–3 per side, occasionally one per side. Type — Reniform. Color — Greenish brown (RHS Grey Brown 199 C).

*Leaf stipules.*—Size — 6 to 9 mm in length. Number — Typically (2) stipules per leaf bud and up to (6) per shoot tip. Form — Lanceolate in form and having a serrated margin.

*Color.*—Green (RHS Green Group 132 A) when young but graduating to a yellow-brown color (RHS Grey Orange Group 177 A) with advancing senescence. The stipules are considered to be early deciduous.

Flowers:

*Flower buds.*—Generally — The floral buds are considered to be medium in size (21–24 mm long) (14–17 mm wide), conic in form, and slightly appressed relative to the bearing shoot.

*Flower buds.*—Color — The bud scales are gray-brown, (approximately RHS Grey Orange Group 177 C). The buds are considered hardy under typical central San Joaquin Valley climatic conditions.

*Hardiness.*—No winter injury has been noted during the several years of evaluation in the Central San Joaquin Valley. The current variety has not been intentionally subjected to drought or heat stress and therefore this information is not available.

*Blooming type.*—Considered average in relation to other peach cultivars commonly growing in the central San Joaquin Valley. Date of full bloom was Mar. 9, 1998.

*Flower type.*—The variety is considered to be a showy type flower.

*Flower size.*—Flower diameter at full bloom is approximately 38 to 42 millimeters.

*Bloom quantity.*—Considered abundant.

*Flower bud frequency.*—Normally 1 to 2 buds appear per node.

*Petal size.*—Generally — Considered medium for the species. Length — Approximately 18 to 20 millimeters. Width — Approximately 16 to 18 millimeters.

*Petal shape.*—Broadly ovate.

*Petal count.*—Nearly always 5.

*Petal texture.*—Glabrous.

*Petal color.*—Light pink when young, (approximately RHS Red Purple Group 62 D), and darkening with advancing senescence to a medium pink (RHS Red Purple Group 67 C). The lower portion of the flower petal is RHS Red-Purple Group 62 A.

*Fragrance.*—None to occasionally slight.

*Petal claw.*—Form — The claw is considered truncate in shape and has a medium size when compared to other similar varieties. Length — Approximately 1.5 to 2.1 millimeters. Width — Approximately 1 millimeter.

*Petal margins.*—Generally considered variable, from nearly smooth, to highly undulate and ruffled, especially apically.

*Petal apex.*—Generally — The petal apices appear slightly domed.

*Flower pedicel.*—Length — Considered medium-short, and having an average length of approximately 1.4 to 1.8 millimeters. Diameter — Considered average, approximately 1 millimeter. Color — Bright green (RHS Yellow Green Group 144 C).

*Floral nectaries.*—Color — Dull, orange to orange-gold (approximately RHS Orange Group 25 B). The color of the nectaries become more dull and slightly darker with advancing senescence.

*Calyx.*—Surface Texture — Generally glabrous. Color — A dull red, (approximately RHS Grey Red Group 181 B).

*Sepals.*—Surface Texture — The surface has a medium length, wooly, and a gray colored (RHS Greyed-Green 198 D) pubescence. Number — Generally 5 per flower. Size — Typically 4–5 mm. wide and 5–6 mm. in length and ovate in form. Color — A dull red (approximately RHS Grey Red Group 182 B).

*Anthers.*—Generally — Average in size. Approximately 1.0 mm in width; and 1.0 to 1.5 mm in length. Color — Red to reddish-orange dorsally, (approximately RHS Grey Purple Group 184 B). Pollen Production — Pollen is abundant, and has a yellow-gold color, (approximately RHS Yellow Orange 19 A).

*Filaments.*—Size — Variable in length, approximately 12 to 16 millimeters. Color — Pale pink/white, (RHS Red Purple Group 69 D), and darkening with advanced maturity.

*Pistil.*—Generally — Average in size. Length — Approximately 15 to 17 millimeters, including the ovary. Color — Considered a very pale green when young, (approximately RHS Yellow Green Group 150 D), and becoming slightly more yellowish with advancing senescence. Surface Texture — Pubescent.

Fruit:

*Maturity when described.*—The present variety of fruit is described, as it would be found in its firm ripe condition at full commercial maturity. In this regard, the fruit of the present variety was first picked on Jul. 3, 1998. The date of last pick of the same fruit in 1998 was approximately July 11 under the ecological conditions prevailing in the San Joaquin Valley of Central California.

*Size.*—Generally — Medium large, and considered uniform.

*Average cheek diameter.*—Approximately 75 to 77 millimeters.

*Average suture diameter.*—Approximately 72 to 75 millimeters.

*Average axial diameter.*—Approximately 77 to 81 millimeters.

*Typical weight.*—179 grams. This is highly dependent on cultural practices, and therefore not distinctive of the present variety.

*Fruit form.*—Generally — Oblate in its lateral aspect. The fruit is generally uniform in symmetry with a slightly oval form when viewed from the apical aspect.

*Fruit suture.*—Generally — The suture appears as a thin line which extends from the base to the apex, and appears slightly deeper, basally, within the stem well, and apically on both sides of the pistil point. No apparent callousing or stitching exists along the suture line.

*Suture.*—Color — The suture normally is the same color as the underlying blush. Both the orange-yellow background, (RHS Yellow Group 13 D) and the red orange color (RHS Red Group 46 A) occur.

*Ventral surface.*—Form — Considered uniform.

*Stem cavity.*—Size — Considered moderately shallow for the species. Width — Approximately 8–11 millimeters. Length — Approximately 21–26 millimeters. Depth — Approximately 6 to 9 millimeters. Form — Considered narrowly oval.

*Fruit base.*—Generally — Considered truncate in form, and uniform.

*Fruit apex.*—Generally — Considered depressed and usually recessed below the height of the apical shoulders.

*Fruit stem.*—Generally — Considered medium in length, approximately 6 to 8 millimeters. Diameter — Approximately 3 to 4 millimeters. Color — Generally a pale yellow-green (approximately RHS Yellow Green Group 145 B).

*Fruit skin.*—Generally — Considered medium or average in thickness. Surface Texture — The variety has very light, short pubescence. Skin Acidity — Considered neutral.

*Tenacious to flesh.*—Yes at commercial maturity.

*Tendency to crack.*—Not observed.

*Skin color.*—Generally — Variable, with approximately 70% to 90% of the fruit surface covered with an attractive red blush.

*Blush color.*—The blush color is generally more prevalent apically. This red blush color ranged from a dark red, (RHS Red Group 46 A) to an orange red, (RHS 47 C), with many degrees of shading and blending occurring between these colorations.

*Skin ground color.*—This is generally present in variable percentages covering approximately 10% to 30% of the fruit's surface. The skin ground color is a yellow-golden (RHS Yellow Orange Group 22 A to 20 D).

*Flesh color.*—Generally — Considered variable from a yellow/orange, (RHS Yellow Orange Group 16 A to 16 D) to reddish orange, (approximately RHS Red Group 45 B). The variable color can radiate into the flesh generally beginning at the exterior margin.

*Flesh fibers.*—Generally — Present, numerous in number, and lightly colored. These fiber are present throughout the flesh.

*Stone cavity.*—Color — Red, (approximately RHS Orange Group 45 B), to a yellow color, (approximately RHS Yellow Group 18 B). With increasing maturity, occasional red flecks can appear randomly in the flesh. These flecks are somewhat lighter in color than the surface of the stone cavity.

*Flesh texture.*—Generally — The flesh is considered firm and fine at commercial maturity.

*Ripening.*—Generally — The fruit of the present variety ripens evenly.

*Flavor.*—Considered very sweet and mildly acidic. The flavor is considered both pleasant and balanced.

*Aroma.*—Pleasant and abundant.

*Eating quality.*—Generally — Considered very good to excellent and well above average when compared to common varieties maturing in the same season.

Stone:

*Attachment.*—Generally — Freestone at commercial maturity.

*Stone size.*—Generally — Considered medium to medium-small for the variety.

*Length.*—Approximately 33 to 35 millimeters.

*Width.*—Approximately 26 to 28 millimeters.

*Diameter.*—Approximately 19 to 21 millimeters.

*Fibers.*—A few medium length fibers are attached along the entire surface of the stone.

*Stone form.*—Generally — The stone is considered oval.

*Stone base.*—The stone base is somewhat oblique.

*Base angle.*—The base angle of the stone is variable, but, most frequently is considered slightly oblique to the stone axis.

*Hilum.*—Generally — Considered medium in size, and relatively well defined. The hilum is approximately 5 to 6 millimeters long and approximately 3 to 4 millimeters wide. Form — Considered oval.

*Apex.*—Shape — The stone apex is raised and has an acute tip.

*Stone shape.*—Considered variable. The stone normally is unequal, although ocassionally may appear nearly equal.

*Stone surface.*—Surface Texture — Generally considered medium in roughness and exhibits substantial pitting laterally. Substantial grooving is apparent over the apical shoulders. Surface pitting is prominent generally, and more frequently, it is present basally. Ridges — Numerous fine ridges are present basally, and converge towards the base of the stone.

*Ventral edge.*—Width — Considered medium, and having a dimension of approximately 4.5 to 6 millimeters at mid-suture with wings most prominent over the basal area.

*Dorsal edge.*—Shape — Full, heavily grooved, and having jagged edges. The dorsal edge is moderately eroded over the apical shoulder.

*Stone color.*—The color of the dry stone is a light to medium brown, (RHS Orange Red Group 31 C).

*Tendency to split.*—Some splitting noted.

*Kernel.*—Form — Oval when fruit is ripe. Length — 18–20 mm. Width — 12–14 mm. Thickness — 3–5 mm. Pellicle — Slight pubescence is present. Color — (RHS Greyed Orange Group 173 B.

*Use.*—The subject variety 'Burpeachfive' is considered to be a peach tree of mid-season maturity, and which produces fruit which are very firm, attractively colored, and which are useful for both local and long distance shipping.

*Keeping quality.*—Fruit has stored well up to 20 days after harvest at temperatures of about 2° C.

*Resistance to insects and disease.*—No particular susceptibilities were noted.

*Shipping quality.*—Well above average.

Although the new variety of peach tree posseses the described characteristics when grown under the ecological conditions prevailing near Fowler, Calif., in the central part of the San Joaquin Vally of California, it will be understood that variations of the usual magnitude and characteristics incident to changes in growing conditions, fertilization, pruning, and pest control are to be expected.

Having thus described and illustrated our new variety peach tree, what we claim is new and desire to secure by Plant Letters Patent is:

1. A new distinct variety of peach tree substantially as illustrated and described and which is characterized principally as novelty by producing an attractively colored freestone Peach which is mature for harvesting and shipment approximately June 27–July 10 under the ecological conditions prevailing in the San Joaquin Valley of Central California.

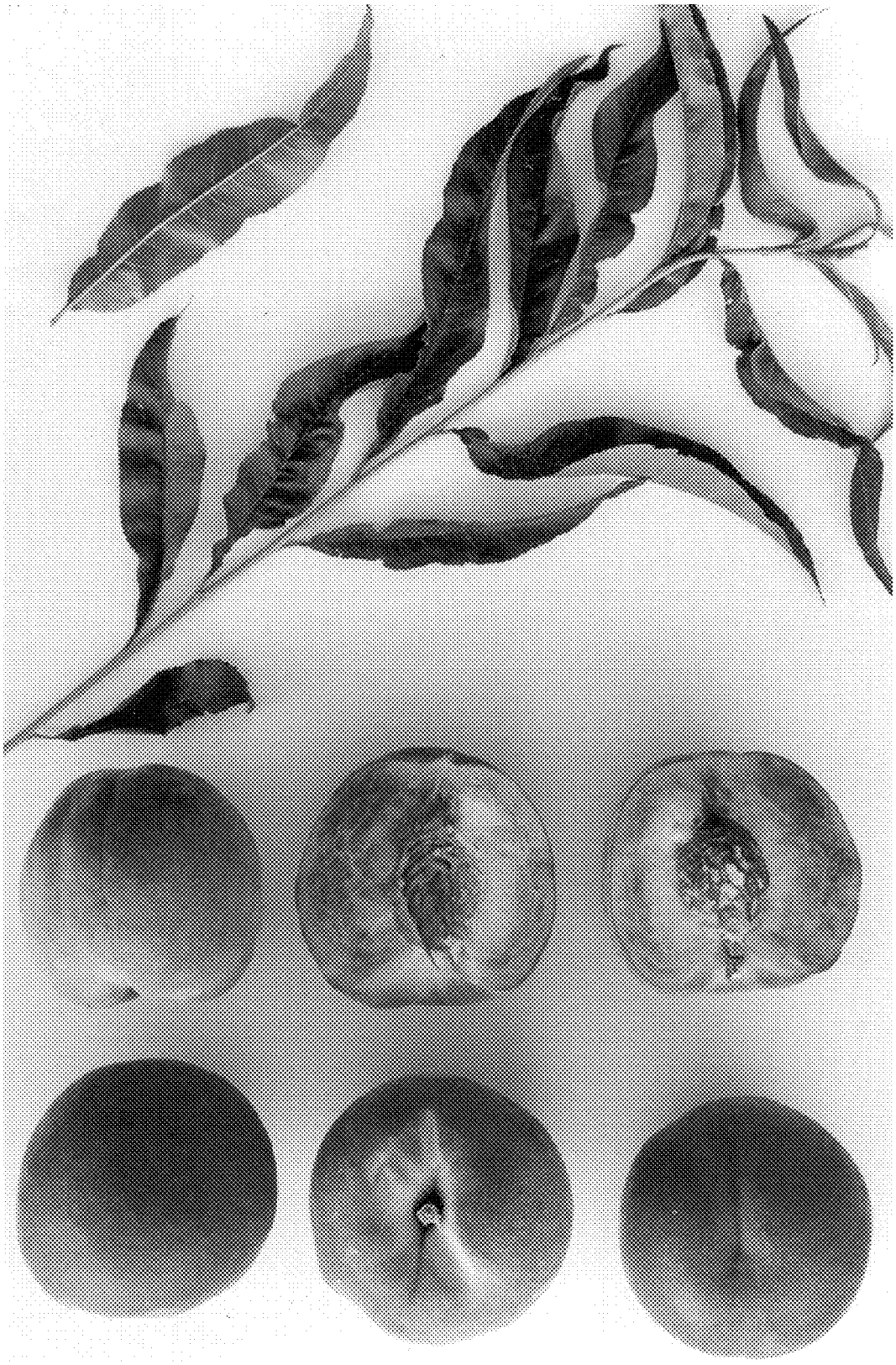

* * * * *